United States Patent [19]

Ramsden et al.

[11] Patent Number: 4,680,120
[45] Date of Patent: Jul. 14, 1987

[54] BONDED PHASE OF SILICA AND CARBOALKOXYALKYL SILANES FOR SOLID PHASE EXTRACTION

[75] Inventors: Hugh E. Ramsden, Scotch Plains, N.J.; Joseph M. Patterson, New Britain, Pa.

[73] Assignee: J. T. Baker Chemical Company, Phillipsburg, N.J.

[21] Appl. No.: 904,892

[22] Filed: Sep. 8, 1986

Related U.S. Application Data

[62] Division of Ser. No. 731,530, May 7, 1985, Pat. No. 4,640,909.

[51] Int. Cl.$^4$ ............................................. B01D 15/08
[52] U.S. Cl. ..................... 210/635; 210/656; 436/178; 436/527; 436/543; 436/816; 436/901; 530/395; 530/413; 530/417; 530/834
[58] Field of Search ............... 210/635, 656, 198.2, 210/502.1; 436/527, 543, 816, 901, 178; 530/395, 413, 417, 834; 55/67, 386; 556/430, 438

[56] References Cited

U.S. PATENT DOCUMENTS

| | | | |
|---|---|---|---|
| 3,935,299 | 1/1976 | Kiselev | 502/407 |
| 4,056,488 | 11/1977 | Mitchell | 502/407 |
| 4,276,061 | 6/1981 | Nestrick | 55/67 |
| 4,324,689 | 4/1982 | Shah | 502/401 |
| 4,329,254 | 5/1982 | Chmielowiec | 502/401 |
| 4,537,759 | 8/1985 | Walker | 55/67 |
| 4,540,486 | 9/1985 | Ramsden | 502/407 |
| 4,578,193 | 3/1986 | Shepherd | 210/198.2 |

OTHER PUBLICATIONS

M. Elsohly et al, Analysis of the Major Metabolite of $\Delta^9$-Tetrahydrocannabinol in Urine, Journal of Analytical Toxicology, vol. 7, Nov./Dec. 1983, pp. 262–264.
D. Black et al, Urine Cannabinoid Analysis: An Integrated Multi-Method Approach, Journal of Analytical Toxicology, vol. 8, Sep./Oct. 1984, pp. 224–227.

Primary Examiner—Ernest G. Therkorn
Attorney, Agent, or Firm—George W. Rauchfuss, Jr.

[57] ABSTRACT

The reaction product of silica gel or controlled pore glass and carboalkoxyalkyl silanes are suitable for use as packing in solid phase extraction columns for cleanup of urine samples for analysis of cannabinoids.

10 Claims, No Drawings

BONDED PHASE OF SILICA AND CARBOALKOXYALKYL SILANES FOR SOLID PHASE EXTRACTION

This is a divisional of co-pending application Ser. No. 731,530, filed on May 7, 1985, now U.S. Pat. No. 4,640,909.

FIELD OF THE INVENTION

This invention relates to solid phase extraction packing material especially such packing material useful for the cleanup of urine samples for analysis of cannabinoids in urine.

BACKGROUND TO THE INVENTION

Detection of marihuana use through analysis of biological samples, such as urine or blood, is coming into more widespread use. Because use of urine samples involves a non-invasive and more convenient process, detection of metabolites of Δ-9-tetrahydrocannabinol in urine has begun to find greater popularity. Additionally, the use of such assay procedure has begun to develop greater importance and more widespread use not only because of its use to initially detect marihuana users but as an adjacent of drug counseling programs as a screening procedure to monitor compliance with withdrawal procedures and continued abstinence from marihuana use.

Of the several metabolites of Δ-9-tetrahydrocannabinol found in urine the major is 11-nor-Δ-9-tetrahydrocannabinol-9-carboxylic acid, hereinafter referred to as THC-COOH, in either its free or conjugated (glucuronide) form. Various non-automated processes exist for detection of THC-COOH in urine, such as thin layer chromatography, gas chromatography, gas chromatography/mass spectrometry, radioimmunoassay, enzyme multiplied immunoassay and more recently high performance liquid chromatography (HPLC). However, such processes are quite labor intensive and due to the numerous and varied interferents in the urine sample are quite cumbersome to carry out. Additionally, it is difficult to measure THC-COOH in urine because of the complex nature of this matrix. The extraction of THC-COOH from urine is rendered more difficult because THC-COOH is one organic acid among a large number and variety of organic acids present in urine. A number of these organic acids have chromatographic properties which are similar to THC-COOH and will interfere with its measurement. Therefore, in order to be able to obtain a meaningful and relatively quick measurement of THC-COOH in urine one must be able to selectively extract it from the urine sample.

Current techniques for screening total urine samples for the presence of THC-COOH are generally either by thin layer chromatography or the Enzyme Multiplied Immunoassay Technique (EMIT) of Syva Company. Once a positive sample is detected a confirmational analysis is performed, usually by gas chromatography/mass spectrometry. However, with adequate cleanup of the urine sample, that is concentration of THC-COOH in the urine sample, and the use of an internal standard, confirmation of HPLC is possible. Thus, a great need exists for a much more satisfactory method of cleanup of urine samples to concentrate THC-COOH present in said samples. A bonded phase chromatographic packing that uniquely and specifically extracts THC-COOH from human urine would be highly desirable. Moreover, a bonded phase that is specific enough for THC-COOH yet permits selective elution of THC-COOH from the column without removing the impurities from the column or selective elution of the impurities from the column without removing the THC-COOH would be most desirable. A bonded phase that provides a purified urine extract clean enough to permit a more sensitive analysis of THC-COOH by confirmational methods, such as by HPLC, is greatly needed. Impure extracts also result in high and noisy baselines that decrease the capability for detecting low levels of THC-COOH. Cleanup of urine samples sufficient to detect low levels of THC-COOH would be most desirable.

BRIEF DESCRIPTION OF THE INVENTION

In accordance with the invention, a bonded phase permitting the extraction of a more highly purified or concentrated form of THC-COOH from human urine is provided by the carboxyl free reaction product obtained from the reaction of silica gel or controlled pore glass, with carboalkoxyalkyl silanes of the formula

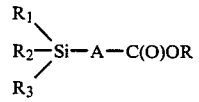

in which R is an alkyl radical of from 1 to 3 carbon atoms, A is an alkylene radical of from about 2 to 4 carbon atoms, and $R_1$, $R_2$ and $R_3$ can be the same or different and are selected from halogen, alkoxy of from 1 to 6 carbon atoms, alkoxy alkoxy of from 2 to 5 carbon atoms and alkyl of from 1 to 3 carbon atoms, with the proviso that at least one of $R_1$, $R_2$ and $R_3$ is a group other than an alkyl group. With such bonded phase silica products one obtains a much purer extract of THC-COOH from urine than from previously used or available bonded phases and this permits quantitation at much lower levels of THC-COOH and also more accurate measurement of THC-COOH. Additionally using this bonded phase a much simpler and more rapid extraction of THC-COOH is obtained.

DETAILED DESCRIPTION OF THE INVENTION

The carboalkoxyalkyl silanes reacted with silica gel or controlled pore glass can be any silane of the hereinbefore set forth formula. In said formula halogen is preferably chlorine, R is preferably methyl and A is preferably ethylene. Most preferably $R_1$, $R_2$ and $R_3$ are methyl or chlorine, most preferably each chlorine. As examples of such silanes to be reacted with silica gel or controlled pore glass there may be mentioned, for example, carbomethoxyethyl trichlorosilane, carbomethylethyl methyldichlorosilane, carbomethoxyethyl dimethylchlorosilane, carboethoxypropyl, trichlorosilane, carbomethoxybutyl trichlorosilane, carbopropoxyethyl trichlorosilane, carbomethoxyethyl trimethoxysilane, carbomethoxyethyl trimethoxymethoxysilane, carbomethoxyethyl triethoxysilane and the like.

The reaction product is useful as a column packing in liquid chromatography for the purification and separation of THC-COOH from human urine especially in high performance liquid chromatography (HPLC) applications.

Such bonded phase silica products are obtained by reaction of silanes of the hereinbefore set forth formula with silica gel or controlled pore glass. The silica gel employed is silica gel having an average particle diameter of from about 3 to about 70 microns and an average pore size of from about 50 to about 1000, preferably about 50 to about 250 Angstrom units.

The particulate controlled pore glass useful as a starting material in this invention is CPG having an average particle diameter is about 37 to about 177 microns and an average pore size of from about 40 to about 1000 Angstrom units.

The silica bonded phase products of this invention are prepared in accordance with the following steps:

A. reacting either particulate silica gel having an average particle diameter of from about 3 to about 70 microns and an average pore size of from about 50 to about 1000 Angstrom units, or particulate controlled pore glass having an average particle diameter of from about 37 to 177 microns and an average pore size of from about 40 to about 1000 Angstroms, in an inert organic solvent slurry, with a carobalkoxyalkyl silane of the formula as set forth hereinbefore, said reaction being conducted as ambient to refluxing temperature for about 2 to about 50 hours;

B. recovering the resultant solid fraction from the reaction mixture; and

C. heating said solid fraction at a temperature and for a time sufficient to dry and completely bond the silane to the respective silica gel or controlled pore glass.

Without being bound thereby, it is believed that the reaction proceeds to completion in two steps as follows, in which a carbomethoxyethyl trimethoxysilane is employed as an exemplary reactant:

Step 1: Silica hydroxyls and the methoxy groups on the silane react to form Si—O—Si bonds and free methanol, with some residual methoxy groups remaining unreacted:

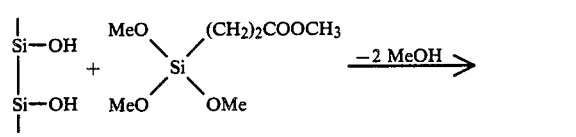

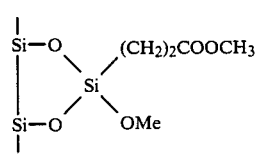

Step 2: Completion of the reaction with the residual methoxy groups is effected during heat curing by (a) and (b):

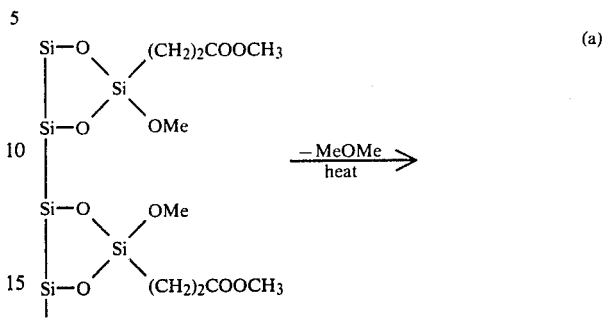

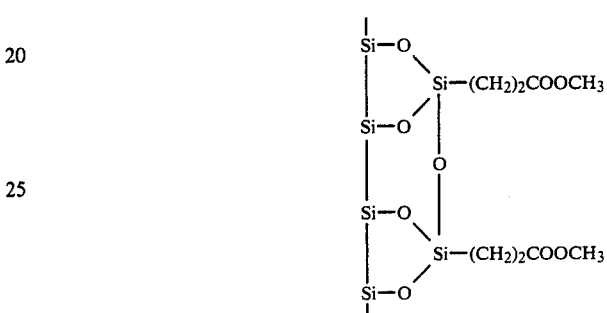

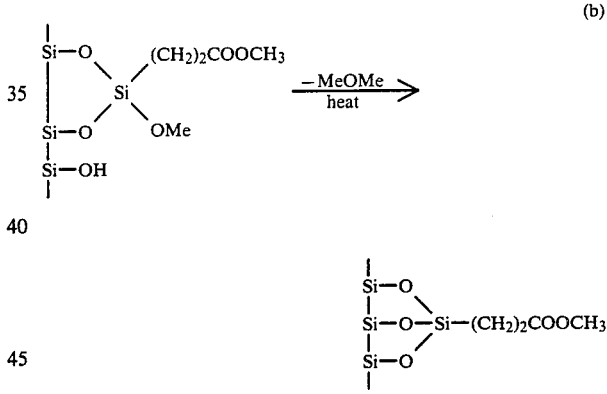

Such products are suitable for use as chromatographic column packing according to this invention. However, it is preferred that such products be end capped, that is, react the unreacted silanol groups with, for example, trimethyl chlorosilane or hexamethyldisilizane in order to render the silanols inert.

Silica gel, consisting of amorphous silica, is commercially available in irregular and spherical particulate forms and in several commercial grades with mesh sizes ranging from 3 through 325 (ASTM). Rather than relying upon a numerical indication of mesh size, however, more accurate indicia for purposes of this invention are the average diameter and average pore size of the silica gel particles, respectively, from about 3 to about 70 microns and from about 50 to about 1000, preferably 50-250 Amgstrom units.

Controlled pore glass (CPG), which is a silicate containing support material chemically similar to silica for use in liquid chromatography, is commercially available, for example, from the Pierce Chemical Co., Rockford, Ill., with average particle diameter of about 37 to about 177 microns and average pore size of, as starting material, about 40 to about 1000 Angstroms, and preferably CPG of about 40 to about 500 Angstroms is employed.

Among the inert organic solvents suitable for preparing the silica gel or CPG slurry are aliphatic hydrocarbons such as, for example, hexane, heptane and the like; aromatic hydrocarbons such as, for example, benzene, toluene, xylene and the like; chlorinated methanes such as for example, methylene chloride, chloroform, carbon tetrachloride and the like; and such other inert solvents as tetrahydrofuran, glyme, diglyme and the like. In general a 1:5 ratio of silica gel or CPG in grams to solvent in milliliters affords a suitable slurry. Due to the fine, insoluble nature of the particulate silica gel and CPG, a slurry rather than a true solution is obtained.

The carboalkoxyalkyl silanes are known or easily prepared. For example, carbomethoxyethyl trichlorosilane is readily prepared by reaction of methyl acrylate and trichlorosilane.

In general, about 25 to about 100 grams of the silane is used to react with each 100 grams silica gel or CPG. The reaction may be conducted to ambient temperature although elevated temperatures up to the refluxing temperature of the reaction solvent system may be utilized to enhance the rate of reaction. The reaction proceeds readily to substantial completion (Step 1) within 2-50 hours. Stirring during admixture of the reactants is advantageously employed although the reaction thereafter may continue without further stirring.

The resultant solid fraction is recovered from the reaction mixture by conventional physical means, for example, filtration, centrifugation and the like. In general, a filtering means sufficient to retain a particle size of 5 microns is suitable whereas centrifuging is suitable for a particle size of 3 microns.

The recovered solid fraction is then heat cured at a temperature and for a time sufficient to dry and completely bond the silane to the silica gel or CPG covalently. In general, from about 1-4 hours to about 40°-120° C. has been found sufficient.

The subject reaction products constitute new and useful bond phases for the purification, concentration and separation of THC-COOH and are particularly suitable for use with solid phase extraction instrumentation. The packing may be of various mesh sizes, for example, from about 50 to about 600 mesh. An example of the methodology suitable for purification and concentration or separation of THC-COOH is similar to that reported in the literature using other but much less effective and efficient bonded phases, for example, the methodology disclosed by M. Elsohyl, *J. Analytical Toxicology,* Vol. 7, pp. 262-264, November/December 1983.

Exemplary of the preparation of the new carboxyl free bonded phases according to the invention are the following representative examples.

EXAMPLE 1

To a slurry of 250 grams of silica (40$\mu$ 60 Å) in 1250 ml of toluene is added 75 ml of carbomethoxyethyl trichlorosilane with stirring. After about 20 minutes of stirring the mixture is allowed to stand for about 20 hours.

The mixture is then filtered, the filter cake product is washed with 2×800 ml of toluene, followed by 2×800 ml of methanol, dried and cured in an oven at about 80° to 85° C. for about 3 to 4 hours.

The product is then end capped by treatment as follows: to 295 grams of product slurried in 1500 ml of toluene is added 80 ml of trimethyl chlorosilane. The mixture is stirred for about 15 to 20 minutes, and let stand for about 2 to 3 hours, then filtered. The product is washed 2×1000 ml toluene and 2×1000 ml methanol, then dried in an oven at about 80° to 85° C. Yield about 300 grams.

EXAMPLE 2

To a slurry of 100 grams of silica gel (40$\mu$ 60 Å) in 500 ml of toluene is added 30 ml of carbomethoxyethyl dichloromethylsilane. The mixture is stirred for about 15 to 20 minutes and allowed to stand for about 16 hours. It is then filtered, washed 2×400 ml toluene and 2×400 ml methanol. The bonded phase is dried and cured in an oven at about 80° to 85° C. for about 3 to 4 hours.

Although this bonded phase product can be used as is for the chromatography, it is preferable to end cap the product.

To the cured product in 500 ml of toluene is added about 15 to 25 ml of trimethyl chlorosilane (or about 10 to 25 ml of hexamethyldisilizane). The mixture is stirred for about 2 to 3 hours, filtered, washed 2×1000 ml toluene and 2×1000 ml methanol, then dried in an oven to about 80° to 85° C.

EXAMPLE 3

To a slurry of 100 grams of silica gel (40$\mu$ 250 Å pore size) in 500 ml of toluene is added 25 ml of carbomethoxyethyl dimethylchlorosilane. The mixture is stirred for about ½ hour, let stand for about 6 to 18 hours, then filtered and washed with 2×400 ml toluene and 2×400 ml of methanol. It is then dried and cured at about 80° to 85° C. in an oven for about 3 to 4 hours.

Usually this bonded phase product does not need to be end capped, but if end capping is desired it can be accomplished in the manner set forth in Example 1.

As exemplary of the use of the bonded phase products of this invention in the cleanup of urine samples for analysis of cannabinoids reference may be had to the following Example. In the following Example the urine sample is first hydrolized to hydrolyze the conjugated form of THC-COOH to free form for chromatographic processing according to this invention. Typically such hydrolysis of a urine sample is conducted in the following manner. Three ml of urine, 3 ml of distilled water and 300 microliters of 10N KOH solution are added to a 15 ml screw top tube. The tube is capped and the solution mixed thoroughly and the tube placed in a 60° C. water bath for about 20 minutes. Following this hydrolysis step the ph of the hydrolysate is adjusted to a ph of 6 with the addition of the appropriate amount of concentrated HCL.

EXAMPLE 4

A standard 3 ml polypropylene solid phase extraction column cartridge (serological grade) is dry packed with 500 mg of the end capped bonded phase from Example 1. The bottom of this cartridge is then friction fitted via Leur type fitting onto a suitable vacuum manifold. The vacuum is then increased to 14 inches of mercury which results in a flow rate of 5 ml/minute. The column is then conditioned to rinse out solubles dry adding two 2 ml aliquots of methanol followed by two 2 ml aliquots of distilled water (care being taken not to let the column run dry during or following conditioning). The vacuum is then turned off. Enough distilled water to fill the cartridge ⅔ of the way is then introduced. A 15 milliliter standard polypropylene (serological grade) reservoir is then friction fitted to the top of the extract column via an adaptor. Five ml of distilled water is then introduced into the column along with the hydrolized urine sample. This entire solution is then aspirated through the column at a flow rate of 5 ml/minute (14 inches of mercury). The reservoir is rinsed with a small portion of distilled water after it has run dry. The extraction column is allowed to run dry and then the reservoir and the adaptor are removed. At this point one observes a colored zone of about 2 millimeters at the top of the cartridge. This zone consists of the extracted THC-COOH as well as a large amount of co-extracted impurities. These impurities are washed from the bonded phase by aspirating through the column at a flow rate of 5 ml/minute two one ml aliquots of 50% acetonitrile/50% 0.1N HCL in water solution. The colored zone at the top of the column is displaced from the column by the first aliquot of the wash solution. The column is allowed to air dry for one minute before the vacuum is turned off. Next, a rack containing a 3 ml glass sample collection tube is placed in the vacuum manifold in such a way that the eluant from the solid phase extraction column is collected. The vacuum is again adjusted so that the flow rate of 5 ml/minute is obtained (14 inches mercury) and three 0.5 ml aliquots of 100% acetonitrile is introduced to the column. Once the column has dried the vacuum is turned off and the sample collection tube containing the concentrated THC-COOH sample eluant is removed from the rack in the vacuum manifold.

If further cleanup is desirable, a 1 ml cyanopropyl bonded phase cartridge (for example, Product No. 7021 available from J. T. Baker Chemical Co. of Phillipsburg, N.J.) can be employed. The eluant from the first extraction cartridge is diluted (1 to 8 dilution) with 0.1N HCL and aspirated through the cyanopropyl cartridge. The column is washed with two 0.5 ml aliquots of a 20% acetonitrile/80% 0.1N HCL solution. The extracted, purified THC-COOH is then eluted from the column with three 100 microliter aliquots of 100% acetonitrile.

The bonded phase of this invention provide a much faster, easier and more efficient sample preparation technique, that is concentration of THC-COOH in the sample, than is possible with heretofore available bonded phases.

We claim:

1. In a solid phase extraction process for the cleanup and purification of 11-nor-Δ-9-tetrahydrocannabinol-9-carboxylic acid from a urine sample, the improvement comprising employing a solid phase bonded silica reaction product of silica and a carboalkoxyalkyl silane of the formula

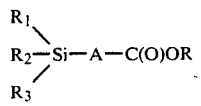

in which R is an alkyl radical of from 1 to 3 carbon atoms, A is an alkylene group of from 2 to 4 carbon atoms and $R_1$, $R_2$ and $R_3$ are the same or different and are selected from the group consisting of halogen, an alkoxy group of from 1 to 6 carbon atoms, an alkoxyalkoxy group of from 2 to 5 carbon atoms and an alkyl group of from 1 to 3 carbon atoms, with the proviso that at least one of $R_1$, $R_2$ and $R_3$ is other than an alkyl group.

2. A process of claim 1 wherein the silica reactant is selected from the group consisting of particulate silica gel having an average particle diameter of from about 3 to about 70 microns and an average pore size of from about 50 to about 1000 Angstrom units, and particulate controlled pore glass having an average particle diameter of from about 37 to about 177 microns and an average pore size of from about 40 to about 1000 Angstrom units.

3. A process of claim 2 wherein the particulate silica gel has an average particle diameter of from about 20 to about 70 microns and an average pore size of from about 50 to about 500 Angstrom units.

4. A process of claim 3 in which the carboalkoxyalkyl silane reactant is a compound in which R is methyl, A is ethylene and $R_1$, $R_2$ and $R_3$ are selected from the group consisting of chlorine and methyl.

5. A process of claim 4 in which the carboalkoxyalkyl silane reactant is selected from the group consisting of carbomethoxyethyl trichlorosilane, carbomethoxyethyl dichloromethylsilane and carbomethoxyethyl dimethylchlorosilane.

6. A process of claim 5 in which the carboalkoxyalkyl silane reactant is carbomethoxyethyl trichlorosilane.

7. A process of claim 1 wherein the silica reactant is particulate silica gel having an average particle diameter of from about 3 to about 70 microns and an average pore size of from about 50 to about 1000 Angstrom units.

8. A process of claim 7 in which the carboalkoxyalkyl silane reactant is a compound in which R is methyl, A is ethylene and $R_1$, $R_2$ and $R_3$ are selected from the group consisting of chlorine and methyl.

9. A process of claim 7 in which the carboalkoxyalkyl silane reactant is selected from the group consisting of carbomethoxyethyl trichlorosilane, carbomethoxyethyl dichloromethylsilane and carbomethoxyethyl dimethylchlorosilane.

10. A process of claim 9 in which the carboalkoxyalkyl silane reactant is carbomethoxyethyl trichlorosilane.

* * * * *